(12) United States Patent
Kohler et al.

(10) Patent No.: US 11,039,737 B2
(45) Date of Patent: Jun. 22, 2021

(54) VIDEO-PROCESSING DEVICE AND VIDEO-PROCESSING METHOD

(71) Applicant: Scholly Fiberoptic GmbH, Denzlingen (DE)

(72) Inventors: Alexander Kohler, Freiburg (DE); Daniel Harter, Freiburg (DE)

(73) Assignee: SCHOLLY FIBEROPTIC GMBH, Denzlingen (DE)

( * ) Notice: Subject to any disclaimer, the term of this patent is extended or adjusted under 35 U.S.C. 154(b) by 0 days.

(21) Appl. No.: 16/720,900

(22) Filed: Dec. 19, 2019

(65) Prior Publication Data

US 2020/0205647 A1 Jul. 2, 2020

(30) Foreign Application Priority Data

Dec. 31, 2018 (DE) .......................... 102018133717.5

(51) Int. Cl.
| | | |
|---|---|---|
| *A61B 1/04* | (2006.01) | |
| *A61B 1/00* | (2006.01) | |
| *A61B 1/05* | (2006.01) | |
| *A61B 1/045* | (2006.01) | |
| *H04N 5/268* | (2006.01) | |

(52) U.S. Cl.
CPC ............ *A61B 1/042* (2013.01); *A61B 1/0005* (2013.01); *A61B 1/045* (2013.01); *A61B 1/051* (2013.01); *H04N 5/268* (2013.01)

(58) Field of Classification Search
CPC ....... A61B 1/042; A61B 1/0005; A61B 1/045; A61B 1/051; H04N 5/268
See application file for complete search history.

(56) References Cited

U.S. PATENT DOCUMENTS 4,646,724 A * 3/1987 Sato ....................... A61B 1/042
 348/68
5,614,943 A * 3/1997 Nakamura ......... H04N 5/23227
 348/72

(Continued)

FOREIGN PATENT DOCUMENTS

DE 102004011629 10/2004
DE 10325382 12/2004

OTHER PUBLICATIONS

Graefe, Volker: Real-Time Image Processing for a Driver-Assistance System for Use on Highways. it + ti—Informationstechnik and Technische Informatik 36 [Computer Science and Computer Engineering], 1, vol. 1/94, special edition Robotics, R. Oldenbourg Verlag, pp. 16-24 (1994).

(Continued)

*Primary Examiner* — Peter D Le
(74) *Attorney, Agent, or Firm* — Volpe Koenig

(57) ABSTRACT

A video-processing assembly (1), particularly for an endoscope, including a video-processing device (2) and an expansion device (3), which is connected to the video-processing device (2) via an interface (14). The interface (14) transmits at least two video data channels (8, 13), a primary video data channel (8) processed in the video-processing device (2) and the secondary video data channel (13) being led unprocessed into the expansion device (3) and processed there. The two processed video signals are combined in a mixing unit (15) in the expansion device (3) and transmitted to an image display device (11).

12 Claims, 4 Drawing Sheets

(56) References Cited

U.S. PATENT DOCUMENTS

| | | | | |
|---|---|---|---|---|
| 6,118,473 | A * | 9/2000 | Tsunezune | H04N 5/23206 348/14.12 |
| 6,246,432 | B1 * | 6/2001 | Takami | A61B 1/00045 348/65 |
| 7,573,536 | B2 | 8/2009 | Paulsen | |
| 10,187,570 | B1 * | 1/2019 | Huang | H04N 5/23293 |
| 2004/0230094 | A1 * | 11/2004 | Nakamura | A61B 1/0005 600/101 |
| 2006/0119621 | A1 | 6/2006 | Krier | |
| 2006/0178558 | A1 * | 8/2006 | Obata | A61B 1/0005 600/109 |
| 2006/0253891 | A1 * | 11/2006 | Wu | H04N 7/181 725/151 |
| 2008/0091065 | A1 * | 4/2008 | Oshima | H04N 19/60 600/109 |
| 2013/0141557 | A1 * | 6/2013 | Kawata | A61B 1/00059 348/65 |
| 2014/0320619 | A1 * | 10/2014 | Nakamura | A61B 1/00013 348/65 |
| 2014/0375781 | A1 * | 12/2014 | Ono | A61B 1/05 348/61 |
| 2018/0018931 | A1 * | 1/2018 | Zhang | H04N 5/268 |
| 2018/0325354 | A1 * | 11/2018 | Saito | A61B 1/00006 |
| 2019/0008373 | A1 * | 1/2019 | Chen | A61B 1/00105 |

OTHER PUBLICATIONS

Siedersberger, Karl-Heinz: Components for Automatic Vehicle Guidance in Seeing (Semi) Autonomous Vehicles, Dissertation, Aerospace Engineering Department, Bundeswehr University Munich, Neubiberg: UniBwM, 2003, Nov. 4, 2003.

Schmidt, Ulrich: Professional Video Technology, 6th Edition, ISBN 978-3-642-38991-7. Berlin; Heidelberg: Springer. Section 10: Video Studio Systems, section 10.5: production units, pp. 762-793, 2013.

Aja: Ki Pro Installation and Operation Guide, Company publication, AJA Video Sytems, published: Nov. 1, 2010, Grass Valley, CA, USA: AJA Video Systems, Inc., Nov. 1, 2010.

Texas Instruments: TMS320DM368 Digital Medial System-on-Chip (DMSoC), Company publication SPRS668C—Apr. 2010—revised Jun. 2011. Dallas, TX, USA: Texas Instruments Inc. 2011.

* cited by examiner

VIDEO-PROCESSING DEVICE AND VIDEO-PROCESSING METHOD

INCORPORATION BY REFERENCE

The following documents are incorporated herein by reference as if fully set forth: German Patent Application No. 10 2018 133 717.5, filed Dec. 31, 2018.

TECHNICAL FIELD

In general, this invention concerns a video-processing device with a video signal input that can be connected to an image-capturing device, a video signal output that can be connected to an image display device, and a primary video data channel with a video signal processing unit in which video signal processing takes place.

BACKGROUND

Video-processing devices of this kind are well-established and can be used, for example, in endoscopy to process image data from a camera head or endoscope, and to make such data available for display on a monitor.

Here, it is also established that different types of cameras can be connected to a video-processing device, for example, 2D cameras and IR cameras or even 3D cameras.

It is now also common practice to combine the connected camera types in such a way that, for example, overlapping can be achieved for visible and infrared images and the required processing steps for three-dimensional stereoscopic display can be achieved using 2D camera heads.

Previously, modular assemblies have been suggested for this purpose, where a number of modules individually achieved each of the desired functionalities.

However, the disadvantage of this approach is that a large number of modules have to be replaced when changing functionality. Alternatively, video-processing devices can be designed such that they contain all of the functionality options, although this makes them expensive and inflexible.

SUMMARY

This invention aims to reduce the effort required in changing functionality.

This challenge is met through the development of a video-processing device designed with one or more features of the invention.

As such, the video-processing device described here is characterised in that the video-processing device has at least one secondary video data channel which branches off from the video signal input and is led out of the device unprocessed. As such, the invention allows for the functionality to be changed in a much simpler way—i.e. using the secondary video data channel—without having to change the core function of the video-processing device as a basic unit. Other functionalities—e.g. using the video-processing device's primary video data channel—can still be used and do not have to be replaced when expanding the device's range of functions.

In essence, the video-processing device can be characterised in that the primary video data channel branches off from the video signal input, leads into the video-processing unit, and is subsequently routed to the video signal output as a processed video data stream.

The video data channels can each be designed as high-speed databases. This enables the use of especially fast video applications.

A demultiplexer, for example, can be attached to the video signal input to separate video signals from multiple video recording devices. In essence, this allows for the device to be fitted with a number of separate primary video data channels. These channels can be processed in one or more video-processing units. The processed video signal(s) can then be routed to one or more image display devices.

Following this invention, it is now possible to include at least one secondary video data channel, which carries data out of the device unprocessed. More specifically, this means that the video signals are not processed in the secondary video data channel. As such, this allows for the raw video data from the video signal input to be routed directly to another point outside the device. The secondary video data channel can, for example, be routed to a separate output, i.e. an output that is separate from that of the primary video data channel.

Where the invention is adapted for this purpose, the primary video data channel also leads processed data out of the device. More specifically, this means that the data stream leaves the device after passing through the video-processing unit.

A more favourable variation of the invention could be designed so as to fit the video-processing device with an interface, through which the secondary video data channel—and preferably also the primary video data channel—is/are led out of the device.

In particular, the interface can be designed to connect to an expansion device. The expansion device, which is described in more detail below, can be used to expand the range of functionalities described above.

Further, it is preferable for the interface to be designed to transmit communication data. This would allow, for example, control signals to be transmitted to an expansion device, e.g. for image control or exposure control.

Where appropriate, the interface can also be designed to transmit configuration data. This would allow, for example, for operating parameters to be interchanged or altered.

Further, where appropriate, the interface can also be designed for power supply. This would allow for an expansion device to be powered through the video-processing device.

An interface of this kind would enable an expansion device to be connected in a simpler way, without a number of additional plug connections.

In particular, it may, where appropriate, be useful for the interface to be designed in such a way that the devices are connected by placing them on top of one another.

Here, it can be beneficial for the interface to be fitted with a mechanical connection point in addition to the electrical connection point. Alternatively or additionally, the video-processing device can also be designed with a mechanical coupling that allows for it to be coupled mechanically to an expansion device.

In a more favourable variation of the invention, the video-processing device would include a detector that detects whether an expansion device has been connected. This could be used, for example, to activate an interface.

Further, in a more favourable variation of the invention, the video-processing device would include a mechanism for updating expansion operating software, which could replace and/or alter the software already used in the video-processing device. This could be done manually, for example.

The invention further comprises an expansion device, featuring a primary video data channel with a video signal processing unit that can be connected via the interface to a secondary video data channel in the video-processing device, as well as a secondary video data channel that can be connected via the interface to a primary video data channel in the video-processing device and that can be connected to a video signal mixing unit that is also connected to the video signal processing unit.

As such, the expansion device itself also features at least two video data channels, of which the primary video data channel contains a video-processing unit, and which can be connected to a secondary video data channel—i.e. an unprocessed video data channel—in the video-processing device.

The expansion device's secondary video data channel leads unprocessed data into a mixing unit. This secondary video data channel is connected to the video-processing device's primary video data channel for processed data. In the mixing unit, the two video data channels may be combined in a number of ways, for example, by being superimposed over one another, next to one another, combined stereoscopically or displayed picture-in-picture.

In this way, the functionality of the video-processing device can easily be supplemented and expanded.

For example, existing 2D video processing can be converted into 3D video processing through the simple addition of the appropriate expansion device. Here, the video-processing device would, for example, process the left image channel, while the expansion device would process the right image channel. In the mixing unit, the 3D image would be combined so that it can be displayed with a 3D image display device.

As such, different expansion devices can be designed for different functionalities, including IR image overlapping, false colour display, and many others. For all types of functionality, the only action that would be required to change functionality would be the addition of the expansion device, meaning that adjustments to the functionality can be carried out simply and efficiently. The data processed in the primary video data channel in the video-processing device can either be left unchanged or included in the overall processing function.

This invention also makes it possible for a cost-effective, basic video-processing device to be expanded at any time. As such, a simple video-processing device can be purchased as a piece of basic equipment and then supplemented at any time without rendering it useless.

In a more favourable variation of the invention, the expansion device can be fitted with a video signal output that can be connected to an imagine display device. This allows the video signal processed and combined in the expansion device to be exported to an image display device.

Alternatively and/or additionally, the expansion device may be fitted with a video signal output that can feed a mixed video signal back to the video-processing device. This allows the video signal that is processed and combined in the expansion device to be fed back into the video-processing device and, in turn, to be displayed on an image display device to which it is connected. This could allow, for example, for the introduction of a new functionality into the expansion device without substantial changes having to be made to an existing video-processing assembly, i.e. by re-plugging cables. This helps to ensure that expansion is very straightforward and can be used by non-qualified personnel.

Where appropriate, the expansion device can feature a video signal input that can be connected to an image-capturing device. This could be used, for example, to add a secondary image-capturing device to enable 3D or stereoscopic image capturing, or to incorporate another spectral range, with the image signal mixing process taking the place of the mixing unit in the expansion device.

In another more favourable variation of the invention, the expansion device is fitted with an expansion interface, which allows for two expansion devices to be coupled together. Here, it is preferable for the interface to be able to accommodate video data channels, control data, configuration data, power supplies and/or other signals. In principle, this could, for example, be used to expand the functionality of an expansion device. However, there may also be the option of connecting the video-processing device to either one expansion device or the other. As such, it would be possible to select which of the expansion functionalities will be used without having to reconnect or replace the expansion devices.

It is particularly beneficial if the power supply for the expansion device is provided by the video-processing device. This removes the need for an additional power connection and simplifies installation.

It is also particularly practical if the interface is designed to connect the video-processing device and the expansion device mechanically and/or if the connection between the video-processing device and the expansion device is a positive connection.

The invention also comprises a video-processing assembly—in particular for an endoscope—with a video-processing device in line with the invention described above and with an expansion device as described above, which is connected to the video-processing device via an interface.

A method for image processing using at least two image channels according to the invention is characterised in that a primary image channel is processed using a video-processing device according to the invention, that a secondary image channel is processed using an expansion device according to the invention, and that the two image channels are combined with one another in the expansion device.

BRIEF DESCRIPTION OF THE DRAWINGS

The invention is described in greater detail below using several examples and with reference to the attached drawings.

The drawings illustrate the following.

DETAILED DESCRIPTION

Figure 1:
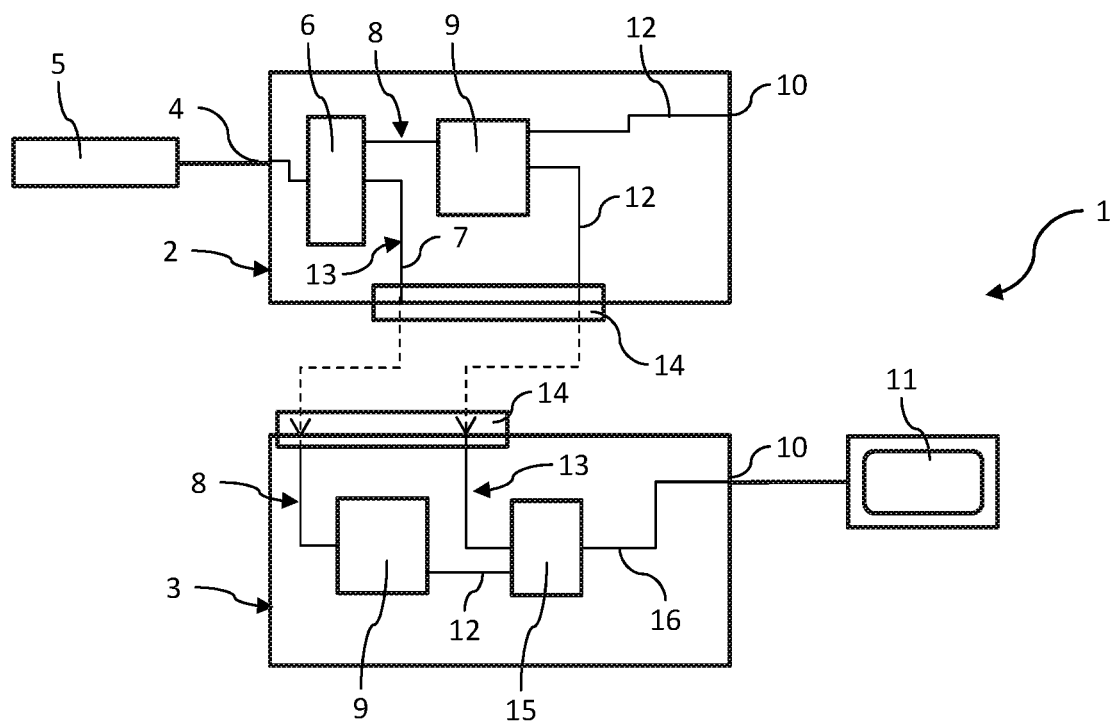
FIG. 1: A video-processing assembly with a video-processing device according to the invention and an expansion device according to the invention.

FIG. 1 shows an initial video-processing assembly 1 according to the invention, with a video-processing device 2 according to the invention and an expansion device 3 according to the invention.

The video-processing device 2 has a video signal input 4, to which an image-capturing device 5 is connected in the example. This image-capturing device 5 could, for example, be a camera head for an endoscope or a video endoscope. However, any other source of video signal can also be connected.

The video signal input 4 is connected internally to a separation unit 6, with two video data channels branching off from the input signal 7. A primary video data channel 8 leads to a video signal processing unit 9. The video-processing device 2 also features a video signal output 10, which is connected internally to the video signal processing unit 9 in order to output the processed video signal 12.

A secondary video data channel 13 connects the input signal 7 directly to an interface 14, where it is then routed outside the device. In the interface 14, the processed video signal 12 from the primary video data channel 8 is also routed outside the device.

The expansion device 3 also has an interface 14, which allows it to be connected to the interface 14 on the video-processing device 2. The expansion device 3 also features a primary video data channel 8, which leads to a video signal processing unit 9. A secondary video data channel 13 leads unprocessed data into a mixing unit 15.

Through the interface 14, the secondary video data channel 13 in the video-processing device 2 is connected to the primary data channel 8 in the expansion device 3, so that the unprocessed input signal 7 from the video-processing device 2 can be transmitted to the video signal processing unit 9 in the expansion device 3. The processed video signal 12 is then transmitted to the mixing unit 15.

Through the interface 14, the primary video data channel 13 in the video-processing device 2 is also connected to the secondary video data channel 8 in the expansion device 3.

In the mixing unit 15, the two video data channels 8, 13 are combined with one another so that a single, mixed video signal 16 can be produced. In the mixing unit 15, the processed video signal 7 from the video-processing device 2 is combined with the processed video signal 7 from the expansion device 3.

The mixing unit 15 is connected internally to a video signal output 10, to which, in the example, an image display device 11 is also connected.

Figure 2:
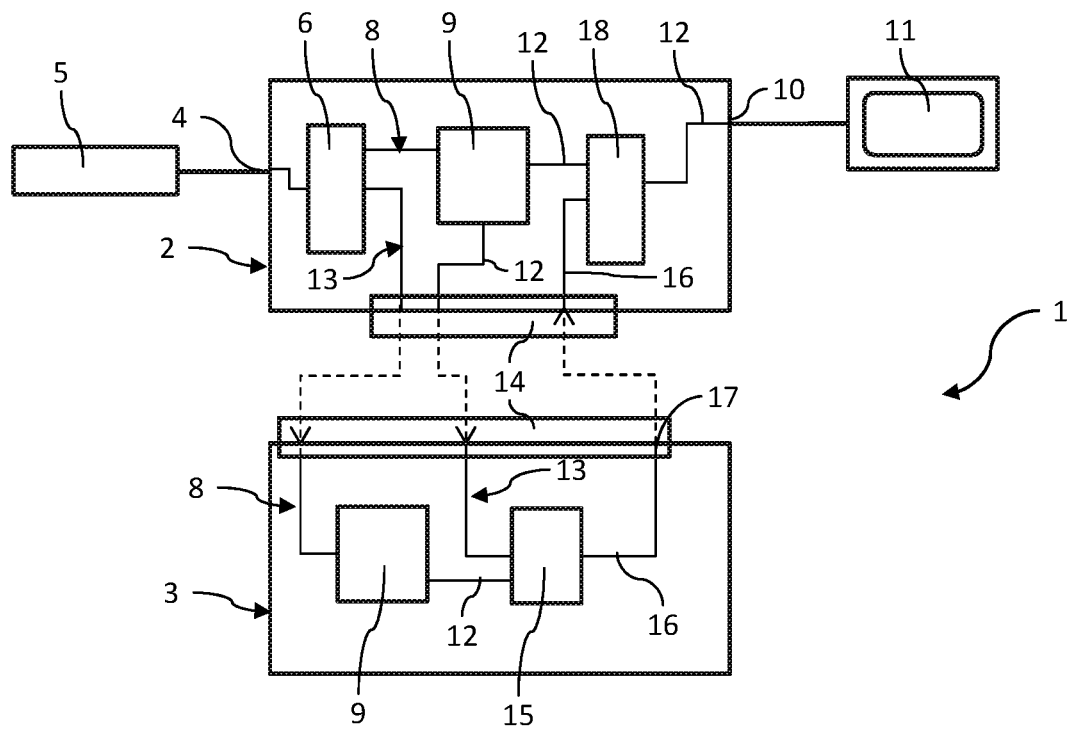
FIG. 2: A further video-processing assembly with a video-processing device according to the invention and an expansion device according to the invention.

FIG. 2 shows a video-processing assembly 1 which is substantively similar to the video-processing assembly 1 shown in FIG. 1.

Additionally, the interface 14 here features a return channel 17 through which the mixed video signal 16 can be fed back to the video-processing device 2. As such, the video-processing device 2 includes a switching unit 18, which allows users to switch the video signal routed to the video signal output 10 between the processed video signal 12 and the return channel 17.

As the mixed video signal 16 is then fed back into the device, the expansion device 3 in this version does not have its own video signal output 10. As such, the image display device 11 is connected to the video signal output 10 on the video-processing device 2.

Figure 3:
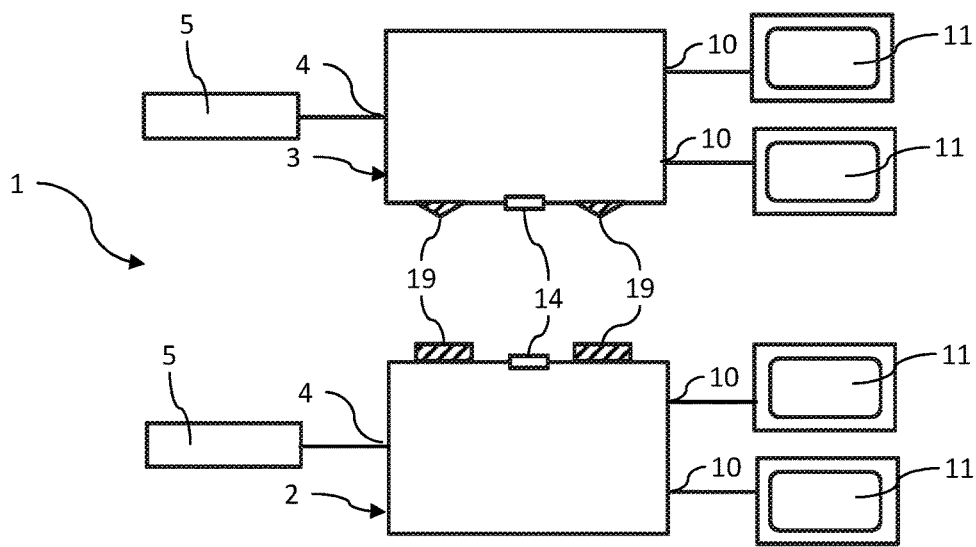
FIG. 3: A third video-processing assembly with a video-processing device according to the invention and an expansion device according to the invention.

FIG. 3 shows another variation of the video-processing assembly 1. Here, the video-processing device 2 features two video signal outputs 10, with an image display device connected to each. In this version, the expansion device 3 also has a video signal input 4, to which an image-capturing device 5 is connected. Using this configuration, the two image-capturing devices 5 can, for example, be designed to allow for stereoscopic data capture or for recordings to be made using different spectra.

In this version, the expansion device 3 also features two video signal output points 10, with an image display device 11 connected to each.

The video-processing device 2 and the expansion device 3 each feature a mechanical coupling 19, which allows for the two devices to be connected together using a positive connection. The coupling 19 can also feature a locking mechanism to prevent the two devices from separating accidentally. This locking mechanism can be designed as a snap lock or as a screw connection, for example.

Figure 4:
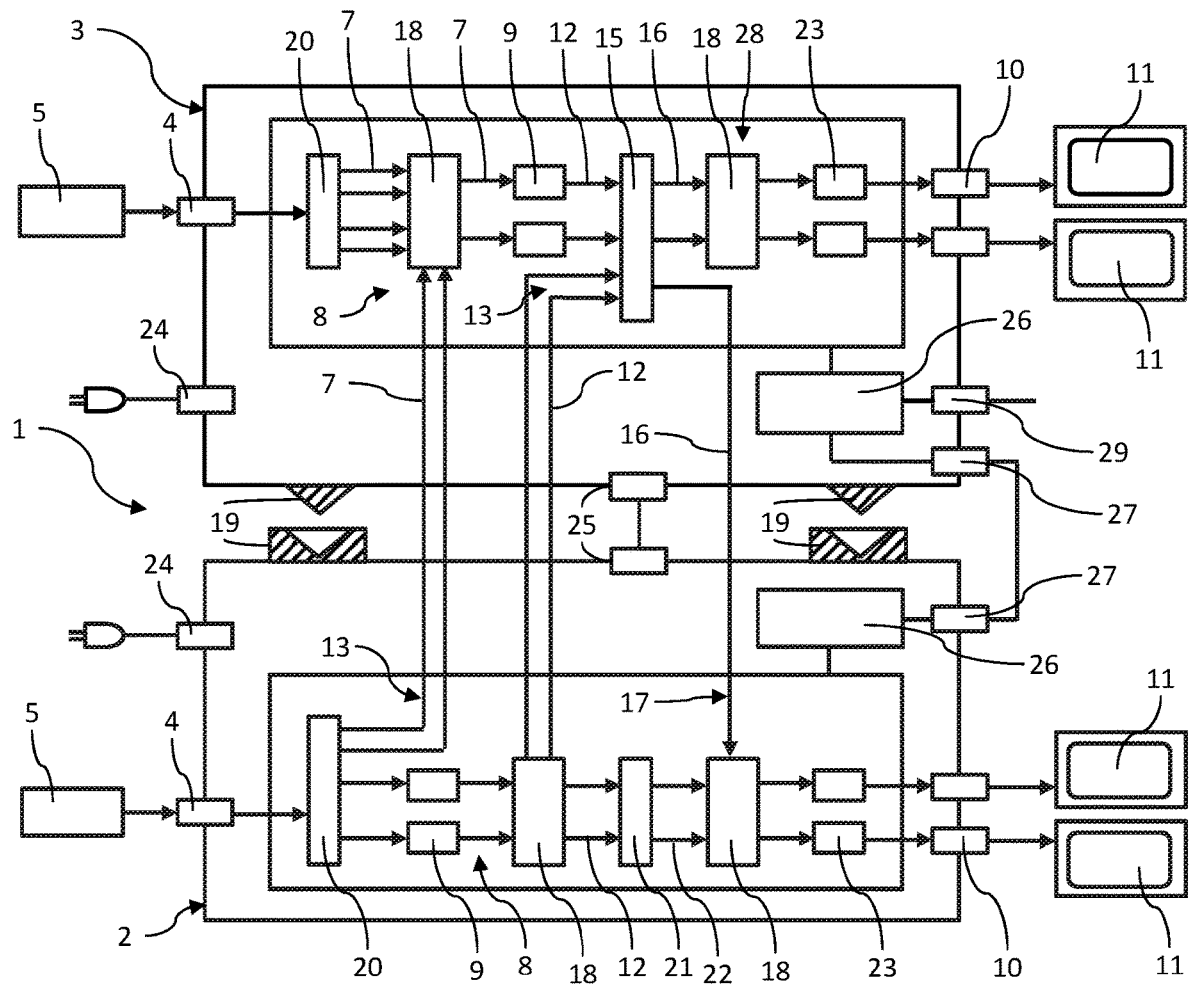
FIG. 4: A detailed view of the video-processing assembly shown in FIG. 3.

FIG. 4 provides a more detailed illustration of the video-processing assembly 1 given in FIG. 3.

The video-processing device 2 has a video signal input 4, to which can image-capturing device 5 can be connected. The video signal input 4 is connected to a demultiplexer 20 as a separation unit, through which the input signal 7 is separated into a number of video data channels. The video signal input 4 can, for example, be fitted with an optical interface, allowing for several video signals to be transmitted by several cameras, with the signals separated into individual video signal streams in the demultiplexer 20.

In this example, the video-processing device 2 has two parallel primary video data channels 8 branching off from the demultiplexer 20. Each video data channel 8 has a video signal processing unit 9 where the video data can be processed.

The processed video signal 12 is routed to a switching unit 18, where the processed video signal (12) can be routed either to an interface 14 or to a computing unit 21. The computing unit 21 can also complete a range of functions, including, for example, side-by-side, picture-in-picture (PIP), picture-over-picture (POP) or overlapping of the two primary video data channels 8. The computed video signals 22 are then routed to another switching unit 18. A return channel 17 in the interface 14 leads to the switching unit 18, so that the user is able to switch between the mixed video signal 16 from the expansion device 3 and the computed video signal 22.

The selected video signal is routed to an output driver 23 and, from there, to a video signal output 10. An image display device 11 is connected to a video signal output 10.

Branching off from the demultiplexer 20 are two secondary video data channels 13, which lead unprocessed input signal 7 to the interface 14 and to the expansion device 3.

The video-processing device 2 also features a power connection 24 through which power can be supplied to the video-processing device 2. The interface 14 also has a power connection 25 to supply power to the expansion device 3 through the video-processing device 2.

If it is not possible or desired for the power to be supplied through the interface 14, the expansion device 3 should also be fitted with its own power connection 24.

The video-processing device 2 features a control unit 26 that controls the individual units. The control unit 26 has non-volatile memory capability, which is used to store an operating programme, and a processor which is used to run the operating programme. The expansion device 3 also has a control unit 26 of this kind, which is connected to the control unit 26 on the video-processing device 2 through a control interface 27. The control interface 27 can also be designed as part of the main interface 14.

Through the control interface 27, the video-processing device can detect whether an expansion device 3 is connected, for example.

In this example, the expansion device 3 also has a video signal input 4, to which an image-capturing device 5 is connected. This video signal input 4 is also connected internally to a demultiplexer 20, from which the two primary video data dreams 8 then branch off. The input signals 7 passed through the demultiplexer are then routed to a switching unit 18. The switching unit 18 is also connected to the interface 14, with the interface 14 connecting the primary video data stream 8 from the expansion device 3 with the secondary video data stream 13 from the video-processing device 2. As such, the switching device 18 allows the user to switch between the input signal 7 and the unprocessed video signal 7 from the video-processing device 2. The primary video data channel 8 leads to a video signal processing unit 9.

The processed video signal 12 is fed into a mixing unit 15. The mixing unit 15 is also connected to the interface 14 through a secondary video data channel 13, with the secondary video data channel 13 connected to the primary video data channel 8 on the video-processing device 2. This means that the processed video signal 12 from the video-processing device 2 is transmitted to the mixing unit 15, where it can be combined with the processed video signal 12 from the expansion device 3.

Here, two 2D images can, for example, be combined to form a 3D image or different camera images can be overlapped, for example by combining an infrared image using false temperature colours with a real image. A large number of other combinations and applications are also possible through the use of an expansion device 3.

The mixed video signal 16 is fed through a return channel 17 to the interface 14, where it is then fed into the video-processing device 2 in the switching unit 18.

Alternatively, the mixed video signal 16 could be transmitted to a routing unit 28 that is connected to output drivers 23, allowing the video signal to be transmitted to the video signal output 10.

The expansion device 3 also features an expansion interface 29, which can be used to attach another expansion device 3. This allows for the range of functionalities included in the video-processing assembly 1 to be expanded further. The expansion interface 29 would preferably be designed as a high-speed data interface, through which video data channels, configuration data and/or control data might be transmitted, for example.

FIGS. 5 to 9 each illustrate a different endoscope assembly 32 featuring a video-processing assembly 1, in which one or two video-processing devices 2 fitted with one or two expansion devices 3 are combined with one another in various ways.

Figure 5:
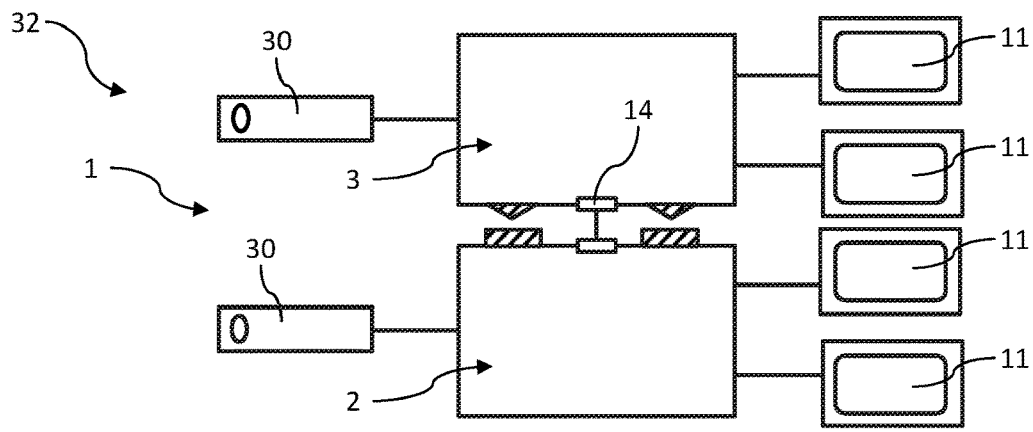
FIG. 5: An endoscope assembly as shown in FIG. 3.

FIG. 5 shows an endoscope assembly 23 in accordance with FIG. 3, where a 2D camera head 30 is fitted to the video-processing device 2 and the expansion device 3. Together, this configuration allows for the creation of 3D images.

Figure 6:
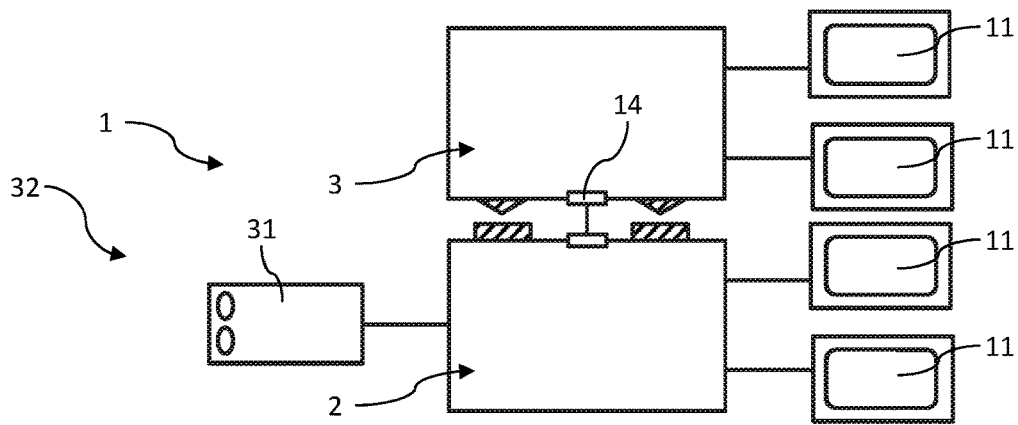
FIG. 6: An endoscope assembly with a video-processing device according to the invention and an expansion device according to the invention.

FIG. 6 shows an endoscope assembly 32 using a 3D camera head attached to the video-processing device 2.

Here, the secondary image channel is processed using the expansion device 3 and used to generate a 3D image.

Figure 7:
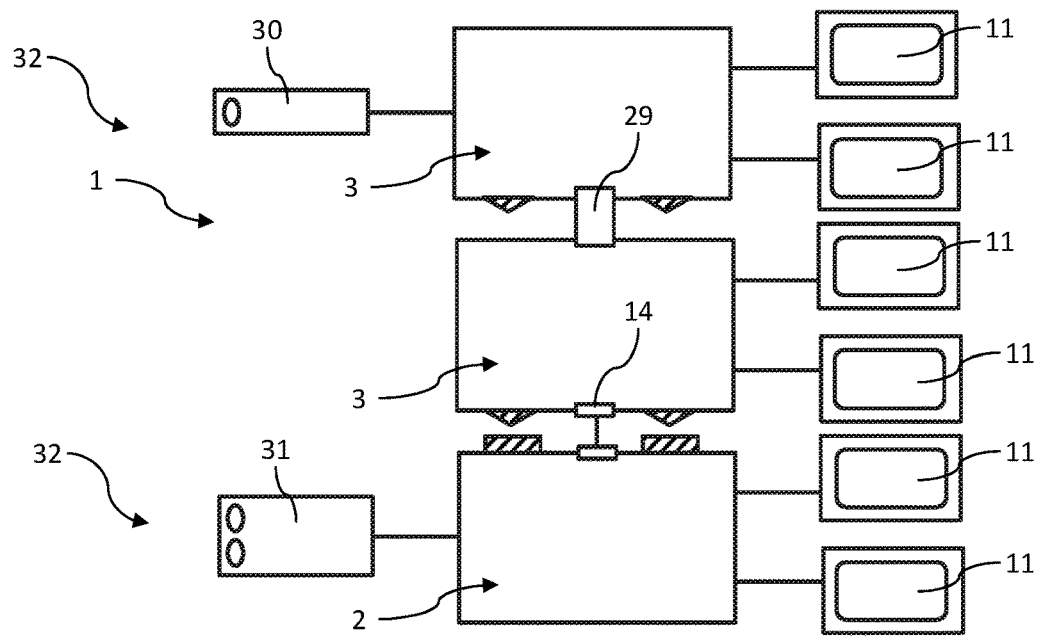
FIG. 7: An endoscope assembly with a video-processing device according to the invention and two expansion devices according to the invention.

With the endoscope assembly 32 illustrated in FIG. 7, the endoscope assembly 32 given in FIG. 6 is further expanded through the use of an additional expansion device 3. A 2D camera head 30 has been attached to this additional expansion device 3. Through the expansion interface 29 on the expansion device 3, video signal from the 2D camera head 20 can, for example, be mixed with the mixed video signal 12 or be displayed separately.

Figure 8:
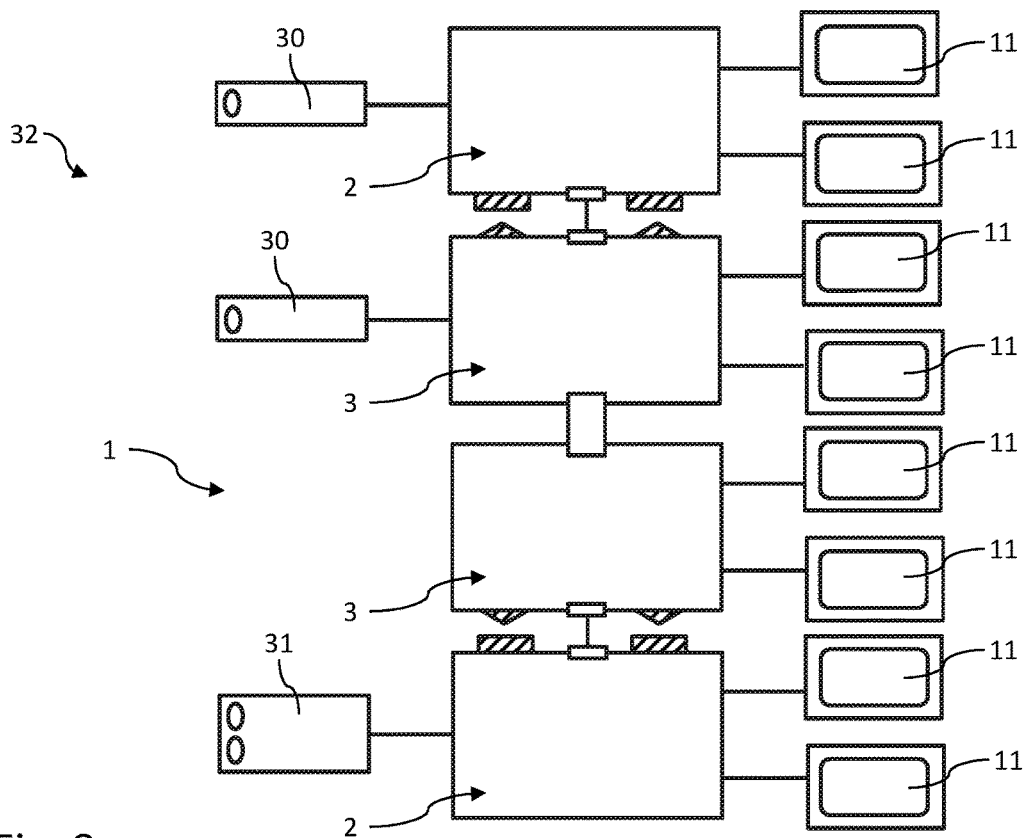
FIG. 8: An endoscope assembly with two video-processing devices according to the invention and two expansion devices according to the invention.

FIG. 8 shows an endoscope assembly 32 with a 3D camera head fitted onto a primary video-processing device 2 that is coupled to a primary expansion device 3. This is, in turn, coupled to a secondary expansion device 3. A 2D camera head 30 is connected to the secondary expansion device. Additionally, the secondary expansion device 3 is connected to a secondary video-processing device 2, which is also connected to a 2D camera head 30. As such, the assembly allows for two independent 3D camera images to be generated, with one of the angles required for 3D imaging being processed in each of the four devices.

Figure 9:
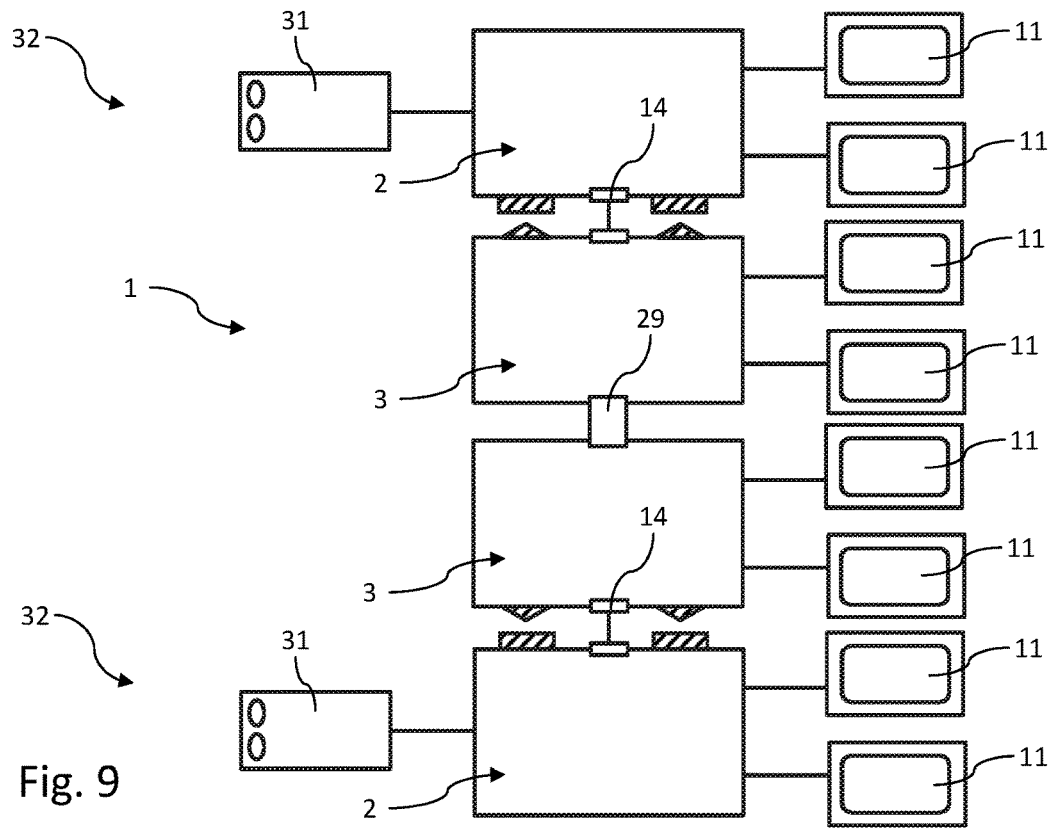
FIG. 9: An endoscope assembly with two video-processing devices according to the invention and two expansion devices according to the invention.

Finally, FIG. 9 shows an endoscope assembly 32 which is similar to that shown in FIG. 8. However, instead of featuring two 2D camera heads 30, a 3D camera head 31 is also connected to the secondary video-processing device 2.

In addition to the variations shown above, it is possible to combine video-processing devices 2 with expansion devices 3 in many other ways. It is also possible to increase the number of video data channels with little effort. These video data channels can be processed in parallel with one another or as alternative options. Additionally, the number of image display devices can be varied depending on the field of application. As such, registration is in no way limited to the specific variations shown here.

LIST OF REFERENCE NUMBERS

1 Video-processing assembly
2 Video-processing device
3 Expansion device
4 Image signal input
5 Image-capturing device
6 Separation unit
7 Input signal
8 Primary video data channel
9 Video signal processing unit
10 Video signal output
11 Image display device
12 Processed video signal
13 Secondary video data channel
14 Interface
15 Mixing unit
16 Mixed video signal
17 Return channel
18 Switching unit
19 Coupling
20 Demultiplexer
21 Computing unit
22 Computed signal
23 Output driver
24 Power connection
25 Power connection on the interface
26 Control unit
27 Control interface
28 Routing unit
29 Expansion interface
30 2D camera head 31 3D camera head
32 Endoscope assembly

The invention claimed is:

1. A video-processing device (2), comprising: a video signal input (4) adapted for connection to an image-capturing device (5); a video signal output (10) adapted for connection to an image display device (11); a primary video data channel (8) with a video signal processing unit (9) configured to process a video signal; at least one secondary video data channel (13) branching off from the video signal input (4) and configured to transmit unprocessed data out of the device; and an interface (14) configured for connection of an expansion device (3), through which the secondary video data channel (13) carries data out of the device and the primary video data channel (8) carries processed data out of the device.

2. The video-processing device according to claim 1, wherein the interface (14) is designed to transmit at least one of: control data, configuration data, or video data channels (8, 13), or to provide a power supply.

3. The video-processing device according to claim 1, further comprising a detector configured to determine when an expansion device (3) is connected.

4. An expansion device comprising an interface (14) that allows for connection to a video-processing device (2), the video-processing device (2) including a video signal input (4) adapted for connection to an image-capturing device (5); a video signal output (10) adapted for connection to an image display device (11); a primary video data channel (8) with a video signal processing unit (9) configured to process a video signal; and at least one secondary video data channel (13) branching off from the video signal input (4) and configured to transmit unprocessed data out of the device,
wherein the primary video data channel (8) with the video signal processing unit (9) of the video-processing device (2) is connected via the interface (14) to an expansion device secondary video data channel (13) in the expansion device, and
the secondary video data channel (13) of the video-processing device (2) is connected via the interface (14) to an expansion device primary video data channel (8) in the expansion device, and
the expansion device includes a video signal mixing unit (15) which is also connected to the video signal processing unit (9).

5. The expansion device as claimed in claim 4, further comprising a video signal output (10) adapted for connection to at least one of an image display device (11) or a video signal output (17) such that a mixed video signal (16) is adapted to be fed back into the video-processing device (2).

6. The expansion device as claimed in claim 4, further comprising a video signal input (4) adapted for connection to an image-capturing device (5).

7. The expansion device as claimed in claim 4, further comprising an expansion interface (29) to which two further expansion devices (3) are coupleable.

8. The expansion device as claimed in claim 4, further comprising a power supply to the expansion device (3) which is enabled through the video-processing device (2).

9. The expansion device as claimed in claim 4, wherein the interface (14) is configured such that the video-processing device (2) and the expansion device (3) are at least one of connectable using a mechanical connection or a positive connection.

10. A video-processing assembly (1), comprising:
a video-processing device (2) including a video signal input (4) adapted for connection to an image-capturing device (5); a video signal output (10) adapted for connection to an image display device (11); a primary video data channel (8) with a video signal processing unit (9) configured to process a video signal; and at least one secondary video data channel (13) branching off from the video signal input (4) and configured to transmit unprocessed data out of the device, and
an expansion device including an interface (14) that allows for connection to the video-processing device (2),
wherein the primary video data channel (8) with the video signal processing unit (9) of the video-processing device (2) is connected via the interface (14) to an expansion device secondary video data channel (13) in the expansion device, and
the secondary video data channel (13) of the video-processing device (2) is connected via the interface (14) to an expansion device primary video data channel (8) in the expansion device, and
the expansion device includes a video signal mixing unit (15) which is also connected to the video signal processing unit (9).

11. An endoscope assembly (32), comprising the image-processing assembly as claimed in claim 10, at least one camera head (30, 31), and at least one image display device (11).

12. A method for image processing that uses at least two video data channels (8, 13), the method comprising:
processing a primary one of the video data channels (8) using a video-processing device (2) including a video signal input (4) adapted for connection to an image-capturing device (5); a video signal output (10) adapted for connection to an image display device (11); a primary video data channel (8) with a video signal processing unit (9) configured to process a video signal; and at least one secondary video data channel (13) branching off from the video signal input (4) and configured to transmit unprocessed data out of the device;
processing a secondary one of the video data channels (13) using an expansion device (3) including an interface (14) that allows for connection to the video-processing device (2),
wherein the primary video data channel (8) with the video signal processing unit (9) of the video-processing device (2) is connected via the interface (14) to an expansion device secondary video data channel (13) in the expansion device, and
the secondary video data channel (13) of the video-processing device (2) is connected via the interface (14) to an expansion device primary video data channel (8) in the expansion device, and
the expansion device includes a video signal mixing unit (15) which is also connected to the video signal processing unit (9); and
combining the primary and secondary video data channels (8,13) with one another in the expansion device (3).

* * * * *